United States Patent [19]
Shantha

[11] Patent Number: 5,195,965
[45] Date of Patent: Mar. 23, 1993

[54] METHOD AND APPARATUS FOR LOCALIZED TREATMENT OF HUMAN VIRAL INFECTIONS AND CANCERS

[76] Inventor: Totada R. Shantha, 1657 Kanawha Dr., Stone Mountain, Ga. 30087

[21] Appl. No.: 665,784

[22] Filed: Mar. 7, 1991

[51] Int. Cl.$^5$ .................. A61M 31/00; A61F 7/12; A61B 17/36
[52] U.S. Cl. ...................... 604/54; 604/114; 606/27; 128/401
[58] Field of Search ............ 604/113, 114, 51–55; 128/399–401; 606/27–31

[56] References Cited

U.S. PATENT DOCUMENTS

| | | | |
|---|---|---|---|
| 2,190,384 | 2/1940 | Newman | 606/27 X |
| 2,734,508 | 2/1956 | Kozinski | 128/401 |
| 3,924,628 | 12/1975 | Droegemueller et al. | 606/23 X |
| 4,754,752 | 7/1988 | Ginsburg et al. | 604/113 X |
| 4,946,440 | 8/1990 | Hall | 604/95 |
| 4,949,718 | 8/1990 | Neuwirth et al. | 128/401 |
| 5,045,056 | 9/1991 | Behl | 604/49 |
| 5,084,044 | 1/1992 | Quint | 606/27 |

FOREIGN PATENT DOCUMENTS 0115407 12/1929 Fed. Rep. of Germany ...... 604/113

Primary Examiner—John D. Yasko
Assistant Examiner—Adam J. Cermak
Attorney, Agent, or Firm—Todd Deveau; Laurence P. Colton; Arthur A. Gardner

[57] ABSTRACT

A method and apparatus for heating the interior surfaces of a hollow organ or orifice of the human body for the treatment of viral infections, microbial infections, and cancers, the apparatus including an insertion body 11 having a semi-rigid support tube 12 and an inflatable balloon 17. Conduits 38 and 39 connect the interior of the inflatable balloon 17 with a heating and pumping unit 31 for heating liquid and circulating liquid within the inflatable balloon to heat the outer surface of the inflatable balloon. For treating infections and cancers, the insertion body is inserted into the organ or orifice and inflated and heated to a selected temperature, e.g., 44° C., and maintained at the temperature for an extended length of time, e.g., for four hours.

7 Claims, 3 Drawing Sheets

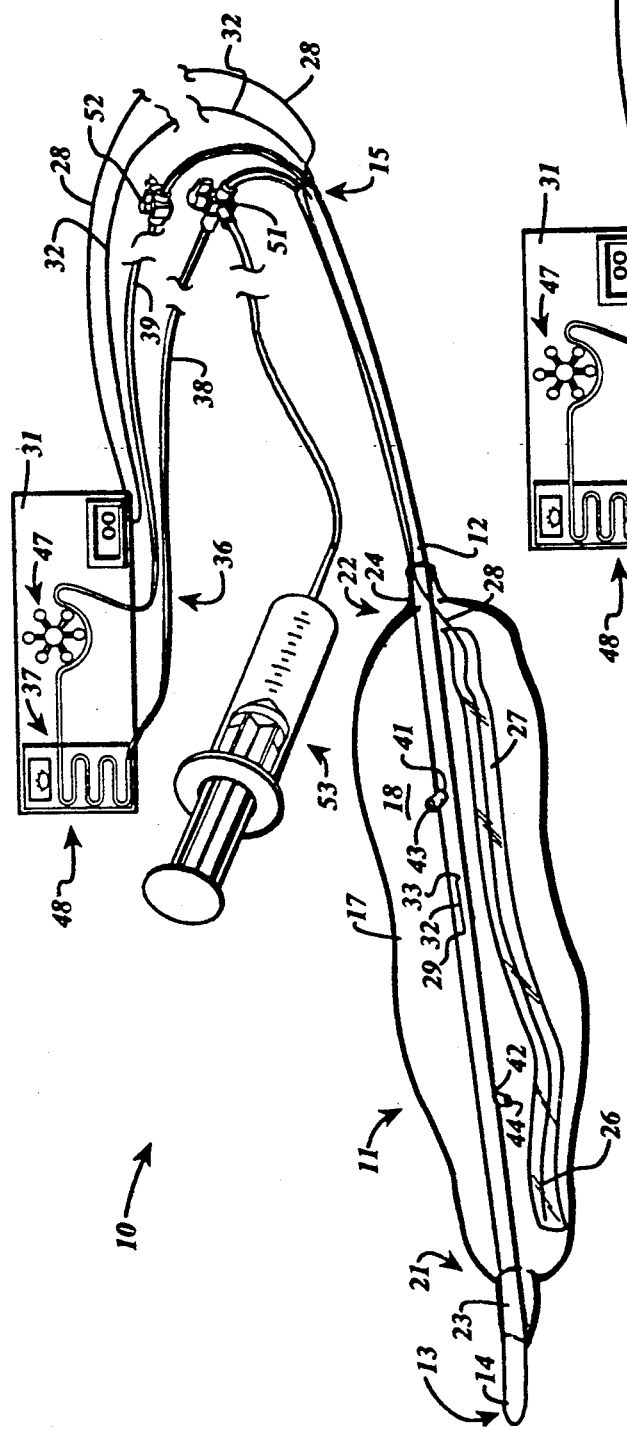
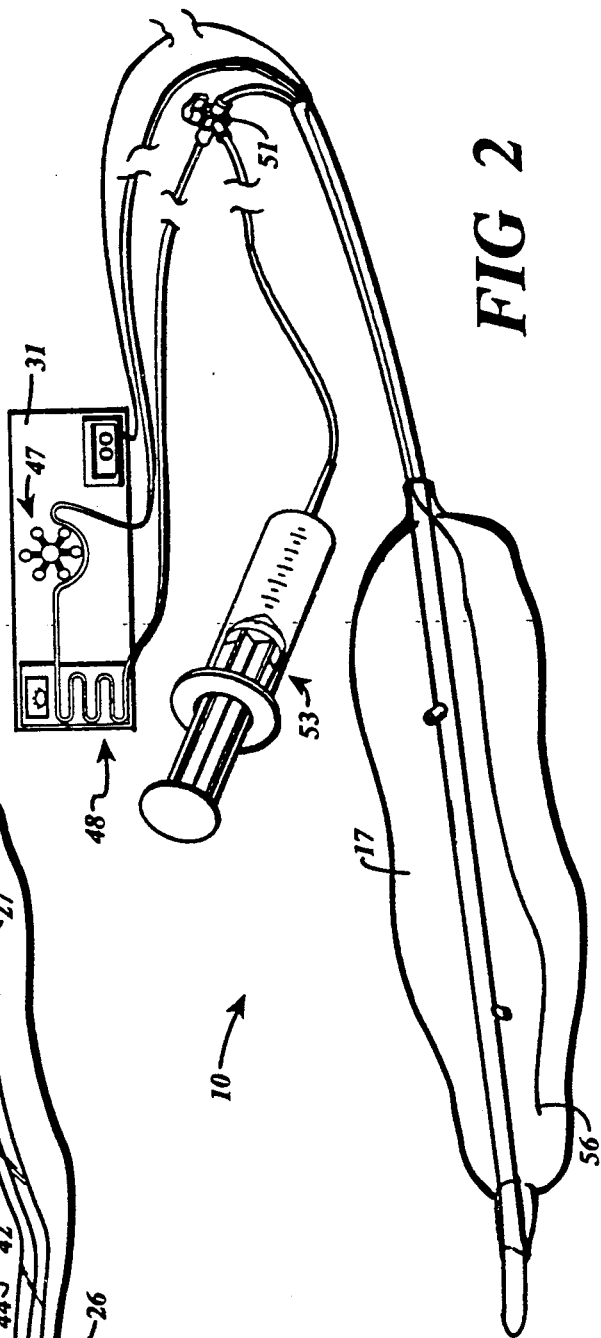
FIG 1
FIG 2

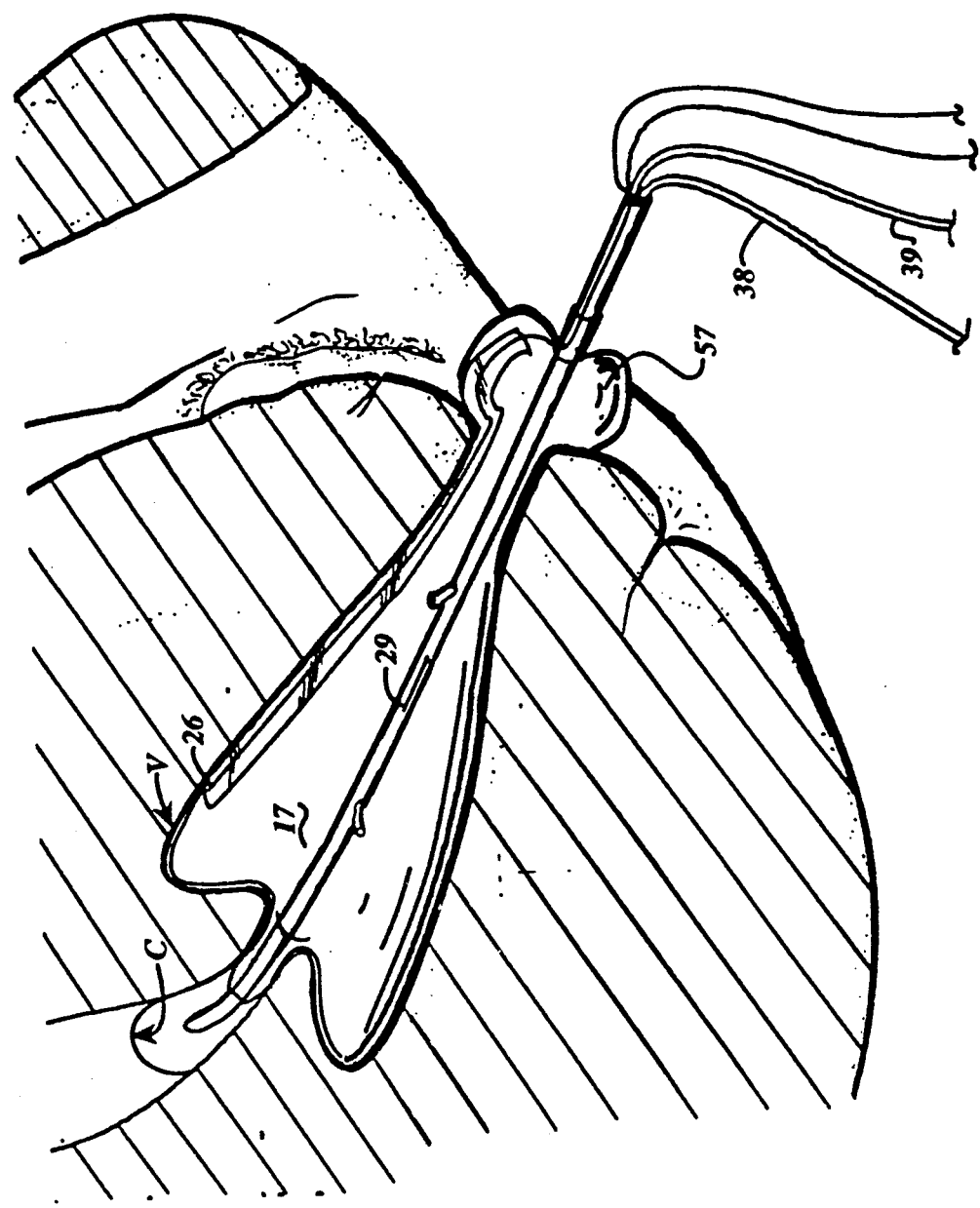

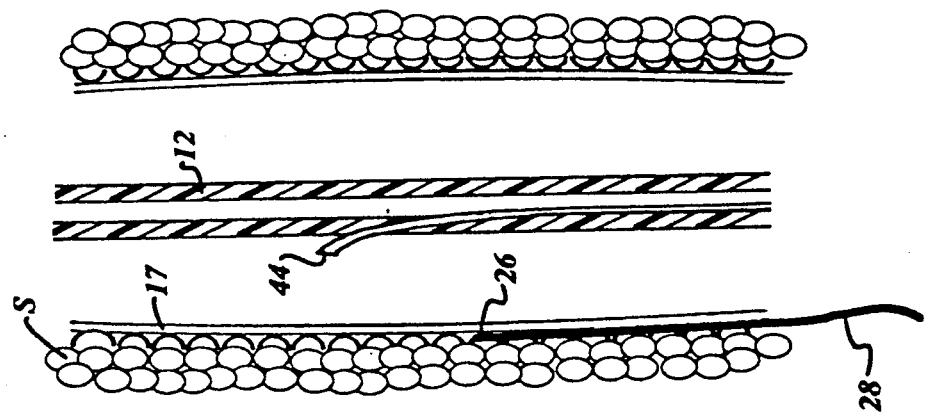

METHOD AND APPARATUS FOR LOCALIZED TREATMENT OF HUMAN VIRAL INFECTIONS AND CANCERS

TECHNICAL FIELD

The present invention relates to a method and apparatus for the localized treatment of human viral infections, microbial infections, and cancers, and particularly infections and cancers of the various orifices and hollow organs of the human body.

BACKGROUND OF THE INVENTION

Viral infections in human beings can be difficult to treat effectively. Indeed, if left unchecked, certain viruses can result in cancer and death. For example, it has been estimated that about twenty percent (20%) of all cancer deaths in women worldwide are from cancers which are associated with the Human Papilloma virus (HPV). It has also been estimated that 90% of all cervical cancer is linked to HPV. While the HPV virus is not the only virus that is linked to cancer or that presents significant treatment difficulties, consideration of the HPV virus provides an excellent backdrop for a discussion of the present invention.

So far, more than fifty-six (56) types of HPV virus have been identified by cloning of the HPV DNA and by hybridization techniques. The HPV virus causes genital warts and is very contagious. It is estimated that there are currently somewhere in the neighborhood of tens of millions of women who suffer from HPV infection of the genital tract. Many of these women end up developing cancer of the cervix and there is no specific therapy which is effective to cure an HPV infection. Currently, HPV is treated with applications of podophyllum, cryotherapy, antibiotics, laser surgery, etc. However, none of these therapies have been found to be satisfactory in eradicating the virus.

It has been known in the medical arts that heat kills microbes and cancer cells. There are cases reported where cancers have disappeared after the development of a high fever. Heating the entire body artificially (total body hyperthermia) has been used as a treatment employing various methods, such as immersing the body in hot water or hot molten wax, or exposing the body to radiant heat. However, total body hyperthermia is mainly limited to use as a treatment of last resort for terminal cancer patients because of the very substantial risk to the patient of death from elevated body temperature. Indeed, total hyperthermia treatment brings to mind the old joke that the operation was a success except that the patient died.

In 1990, much media attention was focused on efforts to cure patients afflicted with deadly Acquired Immune Deficiency Syndrome (AIDS), which is known to be viral, by extracorporeal circulation (heating the blood outside of the body). Successful results of such efforts will likely be limited by the fact that the AIDS viruses are known to reside in many other parts of the body besides the bloodstream. Thus, this approach to the AIDS problem fails to treat significant components of the AIDS virus in the body.

Laser beams, microwave energy and other heating methods have been used locally to kill tumors rather than heating the entire body. However, these techniques also tend to damage healthy tissue. Typical known local heating devices kill at the site of contact and are adapted for either treating external cancers or for treating a specific limited situs of a cancer inside the body. These devices are poorly suited to heating entire hollow organs to eliminate viruses. This is so because the devices generally are not adapted for heating the hollow organ for a long period of time, as may be necessary to kill viruses, and are not well suited to treating the complex and often extensive surfaces of hollow organs safely. For example, there are presently no known devices or methods for heating the esophagus to kill esophageal cancer cells.

In a recent study, 24 women with subclinical HPV infection were treated with an extensive $CO_2$ laser procedure wherein the epithelium (the surface layer of the mucous membrane) of the entire lower genital tract was vaporized. This procedure was costly and quite painful for the patients and resulted in many complications. Only one of the 24 patients was cured of the HPV infection.

Accordingly, it can be seen that a need remains for a method and apparatus for treating viruses and cancers in hollow organs and orifices by heating the infected or cancerous cells, while minimizing pain, collateral injury to surrounding tissue, and the risk of death. It is to the provision of such a method and apparatus that the present invention is primarily directed.

SUMMARY OF THE INVENTION

The present invention comprises an elegantly simple solution to the above-identified problem and involves a recognition that certain viruses, microbes, and cancers do not reside in the entire body, but rather that these certain viruses, organisms, and cancers reside only or primarily in the vicinity of surface regions of hollow organs and orifices.

In a preferred form, the present invention comprises an apparatus for heating the interior surfaces of a hollow organ or orifice, for example the interior surfaces of the reproductive tract of a female human being, for the treatment of viral infections and cancers. For example, the invention is useful for the treatment of Human Papilloma Virus, chlamydia, trichomonas vaginitis, vaginal yeast infections, gonococcus, rectal and anal infections, rectal and anal cancers, esophageal cancer, etc. The apparatus comprises an insertion body having a flexible outer surface and is adapted for insertion into the hollow organ or orifice, such as the female reproductive tract. The insertion body is adapted to contact and conform to the interior surfaces of the hollow organ. The apparatus also includes means for heating the outer surface of the insertion body and for maintaining a selected temperature at the outer surface.

Preferably, the insertion body comprises an inflatable outer membrane or balloon supported about a semi-rigid support member. The inflatable balloon is adapted to contain liquid under pressure and the apparatus includes means for circulating liquid between the inflatable balloon and an external heating device. Sensor means are positioned along the outer surface of the inflatable balloon for determining the temperature of the outer surface of the balloon. Control means, responsive to the temperature of the outer surface as determined by the sensor means, are provided for controlling the external heating device so as to maintain the temperature of the outer surface at the selected temperature.

With this construction, the inflatable balloon can be inserted into the hollow organ in an uninflated state and subsequently inflated with liquid under pressure. The liquid is then circulated and heated in the external heating device. The liquid, preferably water, is maintained at a temperature of between 40° C. and 44° C. for between 2 and 6 hours. Preferably, the water is maintained at a temperature of 41.8° C. (roughly 107.2° F.), and the inflatable body is maintained in the hollow organ for four (4) hours. Maintaining the inflatable body at 41.8° C. for four (4) hours kills many bacteria, viruses and cancer cells. The immune system of the patient normally is stimulated by the destroyed virus cells, microbes, and cancer cells and attacks any infected or cancerous cells not destroyed by the heat. This temperature of 41.8° C. is low enough that healthy tissue survives relatively undamaged, owing to the lesser heat sensitivity of healthy cells as compared with infected and cancerous cells. The localized nature of the treatment, together with the relatively low temperature involved, ensures that the risk of death to the patient from an elevated body temperature is substantially zero. The rather low temperatures involved also protect the patient from much pain and discomfort during treatment.

Accordingly, it is an object of the present invention to provide a method and apparatus for treating cancerous or infected hollow organs or orifices.

It is another object of the present invention to provide a method and apparatus for treating infected and cancerous hollow organs and orifices while minimizing the risk of death from an elevated overall body temperature.

It is another object of the present invention to provide a method and apparatus for treating infected and cancerous hollow organs and orifices which is effective for heating substantially all of the interior surface of the hollow organ or orifice.

It is a further object of the invention to provide a method and apparatus for heating hollow organs and orifices to destroy infections and cancers while avoiding collateral injury to surrounding healthy tissue.

It is yet another object of the invention to provide a method and apparatus for treating infected and cancerous hollow organs and orifices which minimizes any pain and discomfort to the patient during treatment.

It is another object of the invention to provide a method and apparatus for treating infected and cancerous hollow organs and orifices at a relatively low cost.

Other objects, features, and advantages of the present invention will become apparent upon reading the following specification in conjunction with the accompanying drawing figures.

BRIEF DESCRIPTION OF THE DRAWING FIGURES

FIG. 1 is a schematic illustration of an apparatus for localized treatment according to a first preferred form of the invention.

FIG. 2 is a schematic illustration of an apparatus for localized treatment in a modified form of the invention.

FIG. 3 is a schematic illustration of the apparatus of FIG. 1 shown in use in treating the reproductive tract of a human female.

FIG. 4 is a schematic, sectional illustration of a portion of the apparatus of FIG. 3.

DETAILED DESCRIPTION

As described briefly above, the present invention comprises a method and apparatus for treating viral infections and cancers in hollow organs and orifices of the body. The invention has application to the treatment of, inter alia, HPV infections, chlamydia, trichomonas vaginitis, vaginal yeast infections, gonococcus infections, rectal and anal infections, rectal and anal cancers, vocal chord polyps, and cancers in various hollow organs such as the esophagus, larynx and stomach.

For the purposes of illustrating the invention, the method and apparatus depicted in the drawing figures is disclosed in connection with treating HPV infections in the female reproductive tract. It is to be understood however that the invention is not limited to treating HPV infections in the female reproductive tract. For treating maladies of other parts of the body, some modifications might be needed; for example, if the invention is to be used to treat the larynx, some means of ventilating (breathing for) the patient should be provided.

A. THE APPARATUS

Referring now in detail to the drawing figures, in which like reference numerals represent like parts throughout the several views, FIG. 1 shows an illustrative apparatus 10 for localized treatment of viral infections and cancers. The apparatus 10 includes an insertion body 11 adapted for insertion into a hollow organ or orifice. The insertion body includes an elongated, semi-rigid support rod or tube 12 made of a slightly flexible, clear tubing. One end 13 of support tube 12 has a rounded, closed tip 14, while an opposite end 15 is open for receiving therethrough fluid conduits and electrical cables, as will be discussed more fully below.

Insertion body 11 also includes a clear, inflatable balloon or bladder or balloon catheter 17 which is adapted to contact and conform to the interior surfaces of the hollow organ to be treated. The balloon 17 has a smooth outer surface 18 for contacting the interior surfaces of the organ. The balloon 17 is rather elongated and is sealed at first and second opposite ends 21 and 22 to the support tube 12 by means of sealing strips 23 and 24 which are adhered, or otherwise permanently fastened, to both the support tube 12 and the ends 21 and 22 of the balloon 17. The sealing strips 23 and 24 are circumferentially fitted about support tube 12. The sealing strips 23 and 24 can be integrally formed with the ends 21 and 22 of the balloon 17. The particular sealing technique disclosed herein for sealing the balloon 17 to the support tube 12 extending therethrough is known in the medical arts and indeed other sealing techniques can be employed as desired.

The balloon 17 is rather elongated to conform to the internal cavity of the female reproductive tract. The balloon 17 is capable of containing a fluid under pressure and is inflatable thereby. When uninflated the balloon 17 assumes a collapsed state suitable for insertion into the hollow organ, in this case into the female reproductive tract including the vagina. The balloon 17 is comprised of a thin membrane of a material selected to have good heat transfer properties.

Mounted on the outer surface 18 of the membrane of balloon 17 is a thermocouple or sensor 26 for sensing the temperature at the outer surface of the balloon, i.e., the temperature at the interface between the balloon's outer surface 18 and the interior surface of the hollow organ being treated with the apparatus. The thermocouple is rather elongated and is secured to the outer surface 18 of the balloon 17 by means of an elongated strip of tape 27. Thermocouple 26 includes an electrical wire indicated at 28, as is well known. Electrical wire 28 runs along the length of the support tube 12 extending outwardly through the balloon 17 so that the electrical wire 28 extends from the end 22 of the balloon 17 to the end 15 of support tube 12. Electrical wire 28 further extends to a heating and control unit 31.

A second thermocouple 29 is positioned inside the balloon 17 along the surface of the support tube 12. The thermocouple 29 is electrically coupled to the heating and control unit 31 by means of an electrical wire 32 which is threaded into the open end 15 of support tube 12 and extends within the length of support tube 12 and emerges through a small opening 33 formed in the support tube 12. Electrical wire 32 is sealed to the opening 33 to prevent water from escaping from within the balloon 17 into the interior of the support tube 12.

A rather long loop of clear flexible surgical tubing 36 extends between the heating and control unit 31 and the interior of the balloon 17 in a manner such that a "loop end" 37 of the tubing is affixed to the heating and control unit, while the "legs" 38 and 39 of the tubing extend from the control unit into the open end 15 of the support tube 12. The legs 38 and 39 extend within the length of the support tube 12 and emerge from within the support tube via openings 41 and 42 formed in the support tube 12. The openings 41 and 42 are closely matched to the diameter of the legs 38 and 39 of tubing to effect a good seal between the tubing legs 38 and 39 and the support tube 12. Furthermore, caulking or other sealing material can be employed to provide a watertight seal at this juncture. The legs 38 and 39 extend outwardly from the support tube 12 through the openings 41 and 42 and terminate at ends 43 and 44. The ends 43 and 44 of legs 38 and 39 are open to allow fluid to pass through the loop of tubing 36.

The loop end 37 of tubing 36 is threaded through a pumping mechanism of a peristaltic pump, as indicated generally at 47. Such peristaltic pumps are well-known for in use pumping blood during heart operations and typically are incorporated into a device which includes a means for heating and refrigerating the blood so as to be able to lower the patient's body temperature to reduce the patient's consciousness for beginning the operation and to reheat the blood to revive the patient's consciousness after the operation is completed. The Present invention does not require the use of refrigeration capabilities; however, the commercially available peristaltic pumping and heating devices can be economically and advantageously employed because of their built-in heating capability. Such a heating mechanism is shown generally at 48 in FIG. 1.

An important advantage of using a peristaltic pump in connection with the present invention is that the liquid never comes in contact with any portion of the peristaltic pump, but rather the working or moving parts of the pump act only on the external surfaces of the tube through which the liquid runs, thereby avoiding a major sterilization problem. This is important because after use, the insertion body 11 and the associated tubing 36 can be disposed of and a new insertion body 11 and tubing 36 can be used for the next procedure. This makes sterilization of the pump much simpler and less costly than if potentially infectious fluids are brought into contact with the pump. This tends to ensure that infection is not passed from one patient to another via the treatment apparatus and methods.

First and second 3-way valves 51 and 52 are disposed along the legs 38 and 39 of the loop of tubing 36 between the heating and control unit 31 and the insertion body 11. Three-way valve 51 is also connected to a means for adding additional fluid, such as a large syringe indicated at 53. Because the loop of tubing 36 is sealed except for its ends 43 and 44, and because the ends 43 and 44 are received within a sealed balloon 17, the addition of more liquid to the loop of tubing increases the pressure within the closed system. As the tubing is rather thick-walled as compared with the flexible balloon, the increase in pressure tends to inflate the balloon 17. Likewise, any decrease in volume of liquid within the closed system tends to decrease the Pressure within the system and to deflate the balloon. Thus, the syringe 53 acting through the 3-way valve provides an effective and simple mechanism for adjusting the Pressure within the balloon 17. Three-way valve 52 is vented into atmosphere at one of its stations and thereby Provides a ready means for bleeding air from within the tube 36 and within the balloon 17 and for relieving pressure from therein as well.

FIG. 2 shows an alternative embodiment in which only one 3-way valve, valve 51, is employed. FIG. 2 also shows the use of only one thermocouple, in this case thermocouple 56 which is positioned within the inside of the balloon 17.

B. OPERATION OF THE APPARATUS

Referring now to FIGS. 1 and 3, operation of the apparatus will be discussed in connection with treating an HPV infection in the female reproductive tract.

Syringe 53 is filled with sterile water and then is attached to 3-way valve 51 as shown in FIG. 1. At this point, the insertion body 11 is uninflated and the balloon is flaccid. The insertion body 11 is inserted into the vagina so that the rounded tip 14 of the semi-rigid support tube 12 lies inside the cervical canal as indicated at C in FIG. 3. The insertion body 11 is then ready to be inflated to conform the outer surface of the balloon to the interior surfaces of the vagina and cervix. Alternatively, the outer surface of the balloon can be treated with a suitable lubricant to allow the balloon to be inserted in an inflated or partially inflated state.

To inflate the insertion body, 3-way valve 51 is operated so that syringe 53 is in fluid communication with leg 38 of the loop of tubing 36. The syringe 53 is then operated to force liquid into the leg 38 of the tubing 36. Preferably, the liquid inserted thereby should be preheated to be comparable to the patient's body temperature to minimize initial discomfort from relatively warm or cool liquid flowing into the balloon 17. Likewise, the insertion body 11 should be heated to body temperature Prior to insertion. As water is added from the large syringe 53 to the loop of tubing 36, the relatively thick walls of the tubing and the relatively thin wall of the balloon limit the expansion to the balloon. Thus, the balloon begins to inflate while the tubing remains relatively unchanged in size. As the balloon inflates, it may be necessary in some circumstances to bleed off entrapped air. For this purpose, 3-way valve 52 can be operated to vent the entrapped air to atmosphere. Three-way valve 52 can then be closed to resume filling or to maintain the internal liquid pressure.

As the balloon 17 is inflated, it conforms to and contacts the interior surfaces of the vagina V and some of the surfaces of the cervix C. In order to ensure complete coverage of the interior surfaces, the insertion body 11 and the balloon 17 are constructed to be greater in length than the typical vagina so that a portion of the balloon and of the insertion body remains external of the vagina. As the balloon 17 inflates, this external portion also inflates to form a slightly bulbous knob indicated at 57 in FIG. 3. The advantage of using a thin membrane balloon in hollow organs and orifices is that the balloon easily and effectively conforms to the shape of the interior surface, thereby providing a means of applying direct heat to substantially the entire interior surface.

With the balloon 17 now properly inflated, the 3-way valve 51 can be operated to close off the syringe 53 from fluid communication with the tubing in preparation for circulating and heating the liquid within the balloon. The peristaltic pump 47 is then operated to begin circulation of the liquid through the tubing, the liquid being drawn in through one of the ends 43, 44 and expelled through the other of the ends 44, 43 of the tubing. With the liquid now circulating within the balloon 17, heating of the balloon via heating of the liquid can commence.

The heating and control unit 31 preferably includes control means for heating the liquid pumped therethrough to achieve a desired or selected temperature within the liquid. Indeed, such heating means to maintain a selected temperature are well-known in connection with peristaltic pumps as described above and further description is not necessary. It suffices to say that the controls of the heating and control unit 31 are adjusted to achieve a desired temperature of, for example, 41.8° C.

Preferably, the water is maintained at a temperature of 41.8° C. for approximately four hours. To maintain the temperature of the liquid at this desired level, it is necessary to determine the actual temperature of the water. To this end, thermocouples 26 and 29 are provided, with thermocouple 29 reflecting the temperature of the water deep within the balloon 17 and thermocouple 26 reflecting the temperature between the outside surface of the balloon 17 and the interior surfaces of the vagina. Because the present invention is directed to heating the interior surfaces of the hollow organ or orifice, the interface temperature between the outer surface of the balloon and the interior surface of the hollow organ is the most relevant temperature to be concerned with. Indeed, the heating element 48 can be controlled in response to this temperature determination alone. In this regard, the base temperature of the water held within the balloon 17 might slightly exceed the interface temperature to a very small extent.

On the other hand, the thermocouple 29 can be used in conjunction with the exterior thermocouple 26 as a sort of backup or safety check to verify that excessive temperatures are not being achieved within the hollow organ or orifice to avoid danger to surrounding healthy tissue. Furthermore, the interior thermocouple 29 can be used alone to determine the liquid temperature within the balloon 17, with this base temperature being used as a close approximation of the interface temperature existing between the outer surface of the balloon 17 and the interior surfaces of the vagina. However, it is preferred that the interface temperature be measured directly between the outer surface of the balloon and the interior surfaces of the organ and that a base liquid temperature be used to verify the reasonableness of the temperature measurement at the interface, for the purpose of providing a maximum margin of safety for the patient from excessive temperatures.

Preferably, the interface temperature is maintained at 41.8° C. for four hours. However, the interface temperature can be maintained at as low as 40° C. for up to six hours and for as great as 44° C. for as little as two hours to achieve the desired result. Extreme care should be taken to avoid allowing the interface temperature to exceed 44° C., because at temperatures of 46° C. and above healthy tissue can be damaged.

Studies on cancer and normal healthy cells have shown that normal cells can tolerate 43° C. temperature for up to six hours without damage and that cancer cells can tolerate the same temperature only for 3 hours. Heat at 43° C. inactivates the chromosomal protein of disease-inflicted cells. At temperatures greater than 45° C., the proteins within cells begin to coagulate. Animal studies have shown that when the hyperthermia is applied locally to tumors, there is a slow absorption of dead tumor cells and their causative agents. This leads to the potentiation of a host immune response causing destruction of the tumor cells and the causative agents both locally and remote from the site of application of heat. Temperature elevation of even 2 to 3 degrees centigrade dramatically stimulates immune system T cells, interferon alpha and gamma. The stimulated immune system acts on the disease-infected cells and the microbes. This results in destruction of the infecting agents, the infected cells and the cancer cells, both locally and at remote areas of the body. Thus, heating with the present invention can cause complete destruction of the causative agents and the disease-inflicted cells, including cancer cells, without harming the healthy cells.

As shown in FIG. 4, the vaginal mucosa which lines the vagina is comprised of a large number of individual squamous cells. For purposes of illustration, the dimensions of the various elements shown in FIG. 4 are distorted somewhat. The squamous cells, such as cell S, lie adjacent the membrane of the balloon 17 with some of the cells coming into direct contact with the balloon. These squamous cells are the cells in which the HPV virus primarily resides and are the cells which need to be heated according to the present invention to destroy the HPV virus.

After the insertion body has been maintained at the selected temperature for the appropriate length of time, e.g., 41.8° C. at four hours, the insertion body is ready to be removed from the vagina. To prepare the insertion body for removal, it is necessary to relieve the pressure within the insertion body to deflate the balloon. To deflate the balloon, one can open the auxiliary 3-way-valve 52 to vent the pressure within the insertion to atmosphere. Alternatively, valve 51 can be operated to provide fluid communication between the syringe 53 and the tubing, and the syringe can be operated to draw fluid out from within the balloon 17, and indeed this method is preferred because it provides a more complete deflation of the balloon which allows the balloon to be withdrawn more easily. The now-deflated and flacid balloon is manually withdrawn along with the rest of the insertion body, and the insertion body, the tubing, and the syringe are all then disposed of.

C. THE HPV VIRUS

1. Basic Properties of the Virus:

Papilloma virus are members of papova virus family, which includes mouse polyoma virus, simian virus 40 (SV 49) and human viruses BK and JC. These viruses are grouped together because all of them have a circular double strand DNA genome surrounded by a polyhedral capsid with 20 faces (Icosahedral). Papilloma virus have a diameter of about 55 nanometers and an icosahedral structure composed of 72 basic sub-units called capsomeres. There is no lipid membrane envelope surrounding the papilloma virus as seen in the AIDS virus. The viral particles contain capsid protein with a molecular weight of about 54,000 daltons. Minor proteins with a molecular weight of about 76,000 daltons have also been identified. The structure of these proteins has not yet been fully identified. An antigenic site is hidden within the viral structure and is revealed by destruction of the viral particles, as by hyperthermia, by localized heating according to the present invention, or by other methods. The disrupted viral particles stimulates the body's immune system, producing antibodies that are cross-reactive with all the human papilloma viruses. This mechanism destroys infected cells that have not been destroyed by heat using the present invention.

2. Papilloma Virus Distribution

Papilloma virus types are found in a variety of vertebrates, including amphibians, reptiles, birds and mammals. In general, each papilloma virus type is specific for a single species, type of epithelium it attacks, and the anatomic location of attack. All papilloma viruses attack epidermal (skin and vaginal) squamous cells called keratinocytes. The only exception to this is the European Elk papilloma virus, which attacks dermal (below the skin) fibroblasts.

In humans, indications are that by using hyperthermia for 3-4 hours, it is Possible to eliminate the infection or eliminate some viruses, and expose the antigen to the antibodies that are circulating in the body so that the immune system attacks the remaining virus and completely eliminates the infection. With the molecular cloning of papilloma virus DNA, it has become possible to analyze and compare various types of HPV. Currently there are at least 56 distinct HPV types. Heating the virus according to the present invention denatures the cells of the virus by destroying the outer shell of the virus. The heat-denatured viruses are picked up by the lymphocytes and macrophages from the subdermis. This stimulates the immune system to generate antibodies. The antibodies, in turn, attack the remaining surviving viruses and eliminate any remaining HPV infection in the rest of the body. Heat also facilitates the exposure of the HPV antigen to the antibodies and helps the immune system's attack on the remaining virus. The heat also denatures (melts), resulting in disassociation of, nucleic acid in a single strand molecule. The body's repair mechanism is then triggered and removes (snips) these denatured viral particles, making the cell healthy again.

3. Classification of HPV

With the molecular cloning of papilloma virus DNA, it has become possible to analyze and compare various types of HPV. Currently, there are at least 56 distinct HPV types, and many new types are being added to the list each year. Table I below lists some of the known HPV types and their oncogenic (cancer-causing) potential.

TABLE 1

| HPV Type | Human Papilloma Viruses | |
|---|---|---|
| | Disease Association | Oncogenic Potential |
| 1 | Plantar and palmar warts | Benign |
| 2 | Common warts | Benign |
| 3, 10, 28 | Juvenile flat warts, intermediate warts, are condylomata | Rarely malignant |

TABLE 1-continued

| HPV Type | Human Papilloma Viruses | |
|---|---|---|
| | Disease Association | Oncogenic Potential |
| 5, 8 | Macular lesions is epidermodysplasia verruciformis and in immune deficiency | High malignant association |
| 6,11, 42-44 | Condylomata accuminata, low grade dysplasia, types 6 and 11 in laryngeal papillomas | Usually benign |
| 7 | Common warts of meat handlers | Benign |
| 9,12,14,15,17, 19-25,36,40 | Macular lesions in epidermodysplasia verruciformis | Rarely malignant |
| 13,32 | Oral focal epithelial hyperplasia (Heck's disease) | Benign |
| 16,18,31,33,35,39 | High-grade dysplasia, invasive carcinoma of genital mucosa | High malignant association |
| 26 | Cutaneous wart in patient with immune deficiency | Unknown |
| 27 | Cutaneous wart in renal transplant recipient | Unknown |
| 29 | Common wart | Unknown |
| 30,40 | Laryngeal carcinoma | Malignant |
| 34 | Nongenital Bowen's disease | Benign |
| 37 | Keratoacanthoma | Benign |
| 38 | One case of malignant melonama | Malignant |
| 41 | Condylomata and cutaneous flat warts | Benign |

Table 1 indicates various types of HPV, and the diseases they cause. HPV 6 and 11 are common types found in benign, flat, exophytic genital warts, and in some low-grade dysplasia. HPV type found in high-grade dysplasia and carcinoma of the genital tract mucosa are HPV 16, 18, 31, 33, 35 and 39, in order of their frequency.

4. Vaginal Mucosa and the HPV Virus

Structurally, the vaginal mucosa is similar to skin except that the vaginal mucosa lacks hairs and certain secretion glands. In general, the papilloma virus infection is limited to the genital sites of the epidermis. Only cells in the basal layer divide. It is quite probable that the papilloma virus gains access to this basal layer and infects these basal cells, which then divide and become keratinocytes. Keratinocytes normally do not divide. They differentiate progressively as cells move outwardly toward the epithelium. Keratinocytes mature, assume a flat shape and keratin becomes highly cross-linked due to production of the protein "Involucrin." Involucrin forms a tough cell envelope as the keratinocytes continue to mature and differentiate. Papilloma viruses tend to induce hyperplasia of the cells in the intermediate cell layers. This is referred to as an acanthosis. The cells infected with HPV show perinuclear vacuolization, nuclear hyperchromatia and convolutions. Such cells are called "koilocytes." Some of the vaginal superficial cells may show synthesis of new viral DNA and high levels of expression of some of the viral genes.

First the virus infects the basal cells. The virus induces the basal cells to proliferate and thus creates hyperplasia seen in intermediate layers of the epithelium. Once the virus enters the basal cells, the viral DNA may undergo a replication leading to a few copies of viral DNA in each infected cell. Over time, the viral DNA replication becomes synchronous with the cell DNA replication. This phase of viral DNA replication ensures that all basal cells maintain a sufficient number of copies to allow the infection to persist, possibly in a latent state.

It is these basal cells infected with virus that should be attacked and eliminated to achieve a cure. If they are not killed by exposing the virus to such a level of heat the virus and cells infected by the virus rupture, then the antibodies attack and eliminate the infection.

As the keratinocytes of the suprabasal (intermediate) layers ascend and undergo final differentiation, the viral genes increase their activity, resulting in viral DNA replication. This is called late or vegetative replication. As the viral capsid protein production continues in the cervix, the subcolumnar basal cells, the suprabasal cells, and the metaplastic (dividing) cells appear to be the target for infection. Because these cells are proliferating, they are exposed to incoming viruses. It is postulated that the subcolumnar reserve cell is the precursor of both endocervical gland cells and squamous cells. Papilloma virus DNA can be found in cervical endocarcinoma and squamous cell carcinoma of the cervix. Thus, it is possible that the infected reserve cells are a common precursor to various types of cervical cancers.

5. Basic Biology of HPV in Cervical Cancer

The DNA of HPV 6, 16 is found in most cervical carcinomas, in the entire spectrum of dysplasia (abnormal cells), and in some entirely benign-appearing flat genital condylomata. Less commonly found DNA material is that of HPV 18, 33, 35, and 39. Viral capsid proteins are detected by group of specific antibodies in low-grade dysplasia. On the other hand, most of the high-grade dysplasia may not show this viral protein. This viral capsid is never seen in invasive carcinoma. This indicates that the normal viral cycle seems to be blocked by high-grade dysplasia and cancer, so that new virus particles are not made within the carcinomatous cells. Once the cell becomes cancerous it creates a kind of biological dead end for the HPV virus. Progression from mild dysplasia to invasive carcinoma involves many steps. It is probably influenced by other etiological factors. Normal cells are usually diploid while virus-infected cells are polyploid. High-grade carcinomas and high-grade dysplasia cells are generally aneuploid. It appears that with multiplication and mutation, the cellular genes activate an oncogenic gene, resulting in progression of the oncogenic process.

HPV DNA is found in the great majority of cervical cancers. In most cases the viral DNA is integrated into the cellular DNA. Roughly ⅓ of tumors also contain unintegrated free viral chromosomes. In contrast, in benign warts, the viral DNA is present as a free molecule. Therefore, this is the reason why local hyperthermia can kill cancerous and viral-infected cells which are sensitive to heat compared to normal cells. Experimental evidence shows that normal cells survive elevated temperatures better than disease-infected cells. Papilloma virus genomes are not only found in cervical cancer tumors but are also found in metastasis in all cell lines that have been established from such biopsies. Recently, they have been found in most colon polyps and cancers.

The viral DNA is actively transferred with the tumor cells. Nonstructural Papilloma virus proteins have been detected by different techniques, such as western blot or immunoprecipitation. HPV DNA replicates in benign lesions. It can be detected at extrachromosomal circular molecules which, in the cancer cells, is linked to cellular DNA sequences. Its integration within the human genome seems to occur randomly.

It has been observed that formation of cervical cancers directly from papilloma-virus-infected cells is a slow process. It is important to remember that the viral infection per se is not an indication of cervical cancer. Human papilloma virus infection occurs at a very early age, whereas tumors usually develop several decades later. Epidemiologic survey data indicates that the prevalence of HPV infection associated with the cancer is seen in at least 10–30% of the cases and other estimates have placed this association as high as 90%. The malignant tumors are monoclonals, indicating they arose from one single cell. Local hyperthermia treatment according to the present invention can eliminate HPV infections quite early, and thus can prevent the development of cancers years or decades later.

Smoking, multiple pregnancies and the resultant immunosuppression occurring during Pregnancy also contribute to the development of normal cervical cells into cancer cells. It has been thought that papilloma virus proteins E6 and E7 play an important role in the progression of dysplasia to carcinoma.

While the present invention has been disclosed in a preferred illustrative form, and particularly in detail in connection with treating HPV infections, it will be apparent to those skilled in the art that numerous changes, additions and deletions may be made to the invention. For example, it is possible to use other means for heating the insertion body, such as electrically-resistive wires placed against the inner surface of the balloon or within the balloon adjacent the support tube. Such and other other modifications are considered to come within the spirit and scope of the following claims.

I claim:

1. A method for heating the interior surfaces of a hollow organ or orifice of a human body for the treatment of a virus or cancer, the method comprising the steps of:
    inserting an insertion body into the hollow organ, the insertion body having a flexible outer surface adapted to contact and conform to the interior surfaces of the hollow organ;
    heating the outer surface of the insertion body to maintain a selected temperature at the outer surface;
    maintaining the insertion body in the hollow organ for a length of time between two and six hours; and
    withdrawing the insertion body from the hollow organ.

2. A method as claimed in claim 1 wherein the step of heating the outer surface of the insertion body comprises heating the outer surface of the insertion body to maintain a temperature of approximately 44° C.

3. A method as claimed in claim 2 wherein the step of maintaining the insertion body in the hollow organ comprises maintaining the insertion body in the hollow, organ for four hours.

4. A method as claimed in claim 1 wherein the insertion body is inflatable and further comprising the step of inflating the insertion body.

5. A method as claimed in claim 4 wherein the step of inflating the insertion body is performed prior to the step of inserting, the insertion body.

6. A method as claimed in claim 1 wherein the steps of heating the outer surface of the inflatable balloon and maintaining the outer surface at the selected temperature comprises heating liquid external of the insertion body and circulating the heated liquid to the insertion body.

7. A method as claimed in claim 1 wherein the step of maintaining the outer surface of the balloon at a selected temperature comprises measuring the temperature at the outer surface of the balloon and controlling the amount of heat delivered to the insertion body in response to the measured temperature.

* * * * *